United States Patent
Brahme (10) Patent No.: US 7,531,818 B2
(45) Date of Patent: May 12, 2009

(54) MULTIPLE ROOM RADIATION TREATMENT SYSTEM

(75) Inventor: Anders Brahme, Danderyd (SE)

(73) Assignee: Radinova AB, Danderyd (SE)

( * ) Notice: Subject to any disclaimer, the term of this patent is extended or adjusted under 35 U.S.C. 154(b) by 367 days.

(21) Appl. No.: 10/581,299

(22) PCT Filed: Nov. 29, 2004

(86) PCT No.: PCT/SE2004/001770

§ 371 (c)(1),
(2), (4) Date: Jul. 25, 2006

(87) PCT Pub. No.: WO2005/053794

PCT Pub. Date: Jun. 16, 2005

(65) Prior Publication Data

US 2007/0131876 A1    Jun. 14, 2007

Related U.S. Application Data

(60) Provisional application No. 60/526,080, filed on Dec. 2, 2003.

(51) Int. Cl.
*A61N 5/00* (2006.01)
*G21G 5/00* (2006.01)

(52) U.S. Cl. .............. 250/492.1; 250/370.11; 250/515.1; 250/369; 250/295; 250/251; 250/363.04; 250/389; 250/370.09; 250/396 ML; 250/492.3; 378/64; 378/65; 378/901; 378/152; 378/19; 378/41; 378/5; 378/98.8; 378/210; 378/98; 378/117; 378/91; 378/205; 313/105 R; 128/920; 600/427; 600/407; 600/426; 600/436; 600/411; 600/130

(58) Field of Classification Search .............. 250/492.1, 250/370.11, 515.1, 369, 295, 251, 363.04, 250/389, 370.09, 396 ML, 492.3; 378/65, 378/64, 901, 152, 19, 41, 5, 98.8, 210, 98, 378/117, 91, 205; 313/105 R; 128/920; 600/427, 407, 426, 436, 431, 411, 130
See application file for complete search history.

(56) References Cited

U.S. PATENT DOCUMENTS 5,349,198 A * 9/1994 Takanaka .................. 250/492.3
5,433,693 A * 7/1995 Ott ................................ 600/1

* cited by examiner

*Primary Examiner*—Jack I Berman
*Assistant Examiner*—Meenakshi S Sahu
(74) *Attorney, Agent, or Firm*—Young & Thompson (57) ABSTRACT

The present invention refers to a radiation system (1) comprising an excentric gantry (100) arranged in connection with multiple treatment rooms (61-68) separated by radiation-shielding separating members (71-78). A movable rotation head (120) is connected to the gantry (100) and is able to move between, and direct a radiation beam (110) into, the treatment rooms (61-68). A simulator head (200-1 to 200-8) is preferably arranged together with the radiation system so it can be used in each respective treatment room (61-68). In such a case, while a first subject (40-1) is being irradiated in a first room (61), a treatment set-up procedure, including correct positioning of subjects (40-2 to 40-8) and irradiation simulation, can simultaneously take place for the other subjects (40-2 to 40-8) in the other treatment rooms (62 to 68).

14 Claims, 11 Drawing Sheets

MULTIPLE ROOM RADIATION TREATMENT SYSTEM

TECHNICAL FIELD

The present invention generally refers to an irradiation system, and in particular to such a system being able to direct a radiation beam into multiple treatment rooms.

BACKGROUND

During the past decades there have been considerable developments within the fields of radiation therapy and diagnosis. The performance of external beam radiation therapy accelerators, brachytherapy and other specialized radiation therapy equipment has improved rapidly. Developments taking place in the quality and adaptability of therapeutic radiation beams have included new targets and filters, improved accelerators, increased flexibility in beam-shaping through new applicators, collimator and scanning systems and beam compensation techniques. Also improved dosimetric and geometric treatment verification methods have been introduced. Furthermore, new treatment planing systems capable of biological optimization of the intensity distribution of the delivered beams are now being available.

Figure 1:
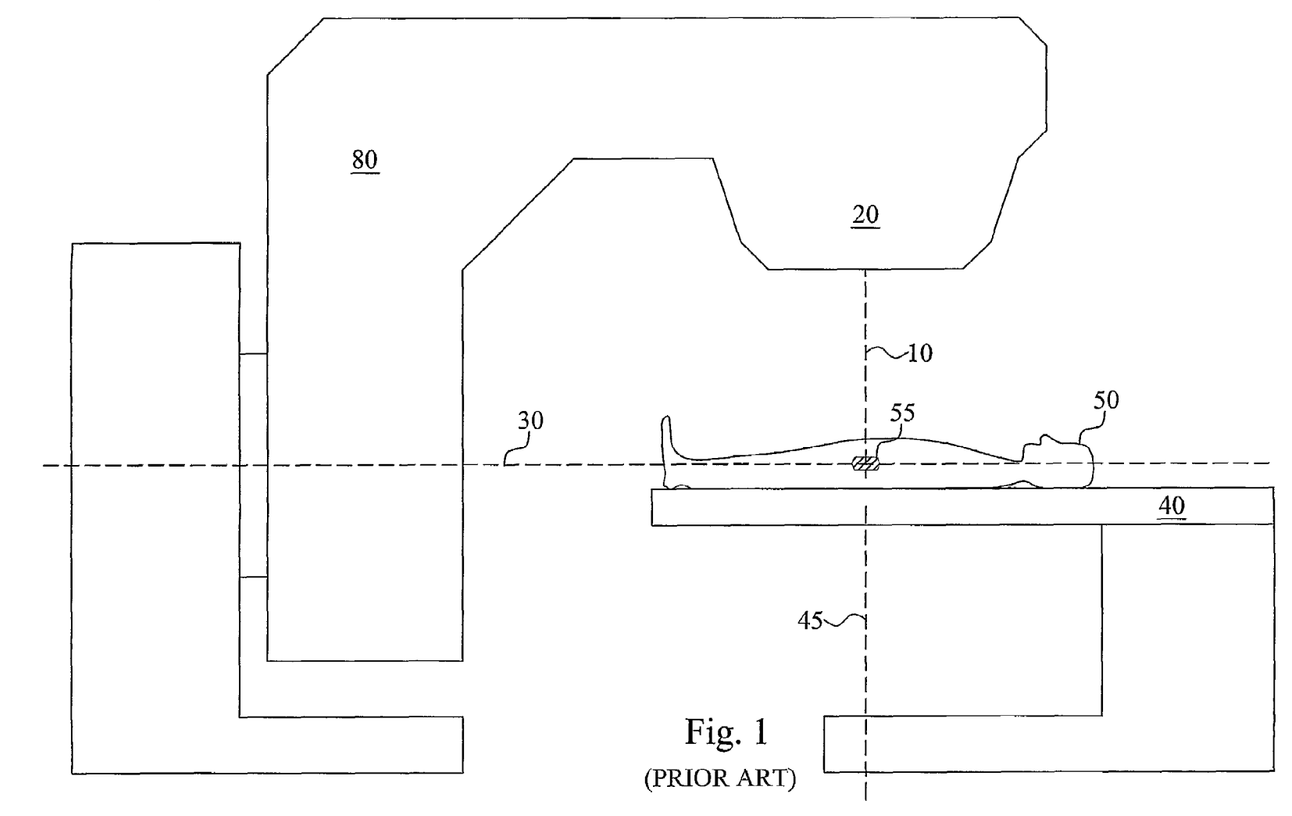
FIG. 1 schematically illustrates a prior art radiation therapy machine with an isocentric gantry design.

In the field of multiple and single fraction radiation therapy and diagnostic imaging, a common general method is to position the patient on a couch. A radiation head and gantry are directing a diagnostic or therapeutic beam onto the patient in order to deliver radiation to a certain target or treatment volume, e.g. a tumor. Such a typical radiation machine according to the prior art is schematically illustrated in FIG. 1. The radiation machine comprises an isocentric gantry 80 designed in a general L shape and a rotational support provided at one axial end of the body of the machine for supporting the gantry 80. Thus, the gantry 80 can rotate around a rotation axis 30 relative the support in order to deliver a radiation beam, schematically illustrated by 10, from a radiation head 20 into a target volume 55 of a patient 50 positioned on a patient couch 40.

Most of the radiation therapy machines of today, including the machine in FIG. 1, comprise an isocentric gantry design. In such a design, the tissue or target volume 55 to be radiated is preferably positioned around a so-called isocenter typically formed by the intersection of three axes at a common point. These axes include the gantry rotation axis 30, the central axis of the radiation beam 10, the major rotational axis 45 of the treatment couch 45, which is also the rotation axis of the collimator head 20 in the figure.

A problem with such prior art radiation therapy machines is their limited capacity in terms of the total number of patients that can be treated in a given time interval. Although the actual irradiation is rather quick, i.e. it typically lasts a few minutes (1-2.5 minutes), a much longer treatment set-up normally precedes the irradiation. During such a set-up, the personnel positions the patient to be treated as accurately as possible, typically based on a treatment plan, which has been developed or compiled earlier based on diagnostic data, radiation beam data, etc. After placing the patient on the couch, but before the actual radiation therapy treatment, a treatment set-up is typically performed to test and verify the beam directions and the treatment plan. In the set-up procedure, the primary aim is setting up the equipment and patient according to the treatment plan. Often portal images, i.e. images based on the treatment beam itself, are used to verify the treatment and monitor its reproducibility. Furthermore, e.g. in vivo dosimetry or related techniques may be used to check the delivered radiation dose in the target volume and/or in adjacent tissues, particularly in organs at risk. If the measured data corresponds to the planed position in the treatment plan, the actual radiation therapy treatment may be safely initiated.

As a consequence of the patient set-up, positioning and simulation procedure, the total treatment takes considerably longer time, generally at least 5-10 minutes and often more, than the actual irradiation. In addition, if some divergence between the measured and calculated data is detected during the set-up and simulation and the divergence exceeds the tolerance margin, the treatment set-up should be adjusted. This may in some cases simply be a correction of some set-up parameters but also larger adjustments requiring a renewed treatment planning process with new anatomical information from a renewed diagnostic procedure. When, a new treatment plan is needed, a renewed treatment simulation may also be needed, increasing the time to treatment by a day or two.

Thus, the time, during which a radiation machine actually is employed for irradiating a patient, constitutes a small portion of the total time, during which the machine is occupied. This of course leads to poor utilization of the costly radiation machines and equipment and that fewer patients can be treated during a given period of time. This problem will be worsen further in cases where the patient undresses in the treatment room, the patient feels uncomfortable and wants to talk to the therapy assistants about various problems with the treatment, etc.

A possible solution could be to perform the simulation procedure using a dedicated radiation simulation machine and not the actual radiation treatment machine. However, although the designs of the patient couches and the two machines used for the simulation and the treatment, respectively, are similar, it may be more difficult to correctly simulate the treatment using a different machine and possibly a different couch top. This is due to problems with positioning the patient exactly in the same way on two different couches, even though the couches may have the same design. In addition, tissue and organs, including the target volume with a tumor, are deformable elastic structures and their positions relative to reference points used in the treatment plan are not rigid, but may change depending on e.g. posture of the patient, filling degree of bladder, respiratory motion, etc. Therefore, although the reference points may be aligned correctly during the treatment relative those during the simulation, the target volume may be misaligned.

In the patent specification U.S. Pat. No. 6,683,318, a therapy system adapted for cancer treatment using light ion radiation beams is disclosed. The therapy system includes an ion source providing light ions to an accelerator system including a synchrotron. An ion beam transport system guides an extracted high energy beam from the synchrotron into three different treatment rooms. In a first treatment room, a static gantry provides horizontal ion beam irradiation. In the remaining two treatment rooms, a respective rotatable isocentric gantry is arranged. Although, this therapy system is using a single ion source and beam accelerator system for the three gantries, the above-identified problems in terms of (low) patient throughput and cost-effectiveness are still present for the individual gantries of the therapy system.

Furthermore, many treatments with charged particles are not made using the isocentric set-up principle, such as during electron, proton or light ion therapy, where generally a fixed SSD treatment with fixed distance between source and patient surface is performed, making isocentric treatment units less important.

SUMMARY

The present invention overcomes these and other drawbacks of the prior art arrangements.

It is a general object of the present invention to provide a radiation system with an excentric gantry.

It is another object of the invention to provide a radiation system with a gantry that can provide radiation beam delivery in multiple treatment rooms arranged around the gantry.

It is a particular object of the invention to provide a radiation system that can direct a clinical radiation beam to a subject in a first treatment room while simultaneously a simulator and beam set-up part of the radiation system is used for irradiation set-up and simulation for other subjects in adjacent treatment rooms as a preparatory process to the irradiation.

It is another particular object of the invention to provide a radiation system having integrated radiation treatment and simulator functionality that can be used in multiple treatment rooms.

These and other objects are met by the invention as defined by the accompanying patent claims.

Briefly, the present invention involves a radiation system or machine with an excentric gantry that can be used for irradiating subjects in multiple irradiation or treatment rooms. With such a gantry it is possible to irradiate, i.e. deliver radiation treatment doses, to a first subject in a first treatment room while simultaneously performing a treatment set-up and simulation procedure for at least a second subject in a second treatment room using the same radiation treatment gantry. When the irradiation of the first subject and the treatment set-up involving the second subject are completed, the gantry can be turned for delivering radiation treatment doses to the second subject simultaneously as a treatment follow-up involving the first subject or a new treatment set-up involving a third subject is performed in the first treatment room. As a consequence, the capacity of the radiation system of the present invention in terms of the total number of subjects to be treated during a given period of time is much larger compared to machines of the prior art. In addition, more time is available for patient care in each treatment room both before and after each treatment occasion.

The radiation system of the invention comprises a gantry adapted for arrangement in connection with multiple treatment rooms separated by radiation-shielding or -isolating separating members, e.g. radiation-shielding partitions (walls) and/or ceilings/floors. A radiation head is mechanically supported by the gantry and is movable relative the gantry between at least a first position for directing a radiation beam into the first treatment room and a second position for directing the radiation beam into the second treatment room.

The gantry of the radiation system is preferably arranged in the intersection of the partitions and/or the ceiling/floor separating the multiple treatment rooms. The radiation system typically has a spherical or cylindrical design, allowing a radiation head to rotate in a dedicated spacing in the partitions and/or ceiling/floor. As a consequence, the radiation head delivering the radiation doses can be turned between the different treatment rooms and therefore irradiate subjects positioned in these different such rooms. The gantry could include a static gantry part attached to the separating members. In such a case, a movable gantry part is movably (rotatably) supported by the static gantry part. The radiation head is then preferably attached to this movable gantry part.

In addition, each treatment rooms preferably comprises or has access to a simulator head with e.g. a light optical and/or diagnostic X-ray system, being able to simulate the therapeutic beam from the radiation head. These simulator heads could be arranged and move concentrically on the gantry. Thus, in each room, the low cost radiation simulator could be used for patient set-up before the radiation head is turned into the treatment room for the real treatment. Alternatively, a few simulator heads could move between rooms and assist in setting up the patient prior to the treatment.

Very many different room configurations can be anticipated from the basic configuration of the radiation system in the partitions and/or ceiling/floor of the rooms. Depending on where a treatment room is located around the central excentric gantry, typically 30-60° oblique lateral anterior, posterior and/or straight vertical and/or horizontal beam directions are possible. It is even possible to use two excentric gantries in such configuration so that multiple treatment portals can simultaneously be directed onto one and the same subject either as oblique lateral, parallel opposed or perpendicular beam combinations.

The excentric gantry of the radiation system of the invention preferably comprises a beam scanning and bending system, such as a magnet-based system, adapted for scanning and bending an incident radiation beam onto a subject in form of a narrow pencil beam. This scanning and bending system, or at least a portion thereof, is then rotated as the radiation head and possibly gantry of the radiation system is turned between different rooms. A bending magnet of the bending system could be laminated to allow fast field changes between accelerator pulses but could also be super-conducting to minimize the bending radius of the magnet.

Due to the design of the bending and scanning system, the excentric gantry is well adapted for usage with light ions from protons and upwards to carbon and oxygen ions, including for example protons, deuterons, tritium and helium, lithium, beryllium, boron, carbon and oxygen ions.

The invention offers the following advantages:

Can be efficiently used for irradiating several subjects in different treatment rooms;

Enables treatment set-up, simulation and/or the subject exit process to be conducted in some rooms while the actual radiation treatment is simultaneously performed in another room;

Increases the capacity in terms of the total number of subjects that can be irradiated during a given period of time;

Enables usage of light ion radiation with a compact gantry design and small bending magnet radius and flexible beam direction selection;

Reduces the installation cost substantially since one low cost device with adjustable beam directions can advantageously be used in multiple treatment rooms instead of multiple expensive isocentric devices with fixed beam line configurations; and Allows full attention to be paid to each patient with regard to individual care and accurate patient set-up without stress for the therapy assistance team.

Other advantages offered by the present invention will be appreciated upon reading of the below description of the embodiments of the invention.

SHORT DESCRIPTION OF THE DRAWINGS

The invention together with further objects and advantages thereof, may best be understood by making reference to the following description taken together with the accompanying drawings, in which.

DETAILED DESCRIPTION

Throughout the drawings, the same reference characters will be used for corresponding or similar elements.

The present invention relates to a radiation system or machine with a so-called excentric gantry design that can be used for providing a radiation beam into multiple, i.e. at least two, irradiation or treatment rooms. The gantry is adapted for arrangement in connection with the multiple treatment rooms, which are separated by radiation-isolating or -shielding separating members. The gantry mechanically supports a radiation head. This radiation head is movable relative the gantry (and the separating members) between different positions for directing a radiation beam into the different treatment rooms.

With such a gantry design it is possible to irradiate, e.g. to deliver radiation treatment doses to a first subject or patient, in a first treatment room while simultaneously allowing preparation for treatment (treatment set-up), simulation or performing treatment follow-up procedure for at least a second subject in another treatment room using the same radiation delivery system and gantry.

As a consequence, the capacity of the radiation system of the invention, in terms of the total number of patients to be treated for a given period of time, is much larger compared to the prior art machines, e.g. the radiation machines of FIG. 1.

In the following the invention will be described with reference to a radiation therapy system, delivering irradiation doses to a patient for the purpose of treatment, and then primarily curative radiation therapy, i.e. to eradicate a tumor. This radiation therapy system could also be employed for palliative radiation therapy, where the aim is generally to improve quality of life of the patient by maintaining local tumor control, relieve a symptom or prevent or delay an impending symptom, and not necessarily to eradicate the tumor. However, the radiation system could alternatively be employed for other radiation purposes, such a single dose radiation therapy, radiation diagnostics or radiation processing. In addition, the radiation system could be used for combined radiation therapy and diagnosis. In the latter case, the radiation head can deliver both a (high-energy) radiation treatment beam and a (low-energy) radiation diagnostic beam. Actually, the radiation system according to the present invention can be applied for any radiation purposes, where it is desired to direct a radiation beam onto an object or patient in a treatment room simultaneously as a radiation simulation, set-up or follow-up is performed in a (neighboring) treatment room involving another object or patient, to be subsequently irradiated or already has been irradiated, using the same radiation gantry.

Figure 2:
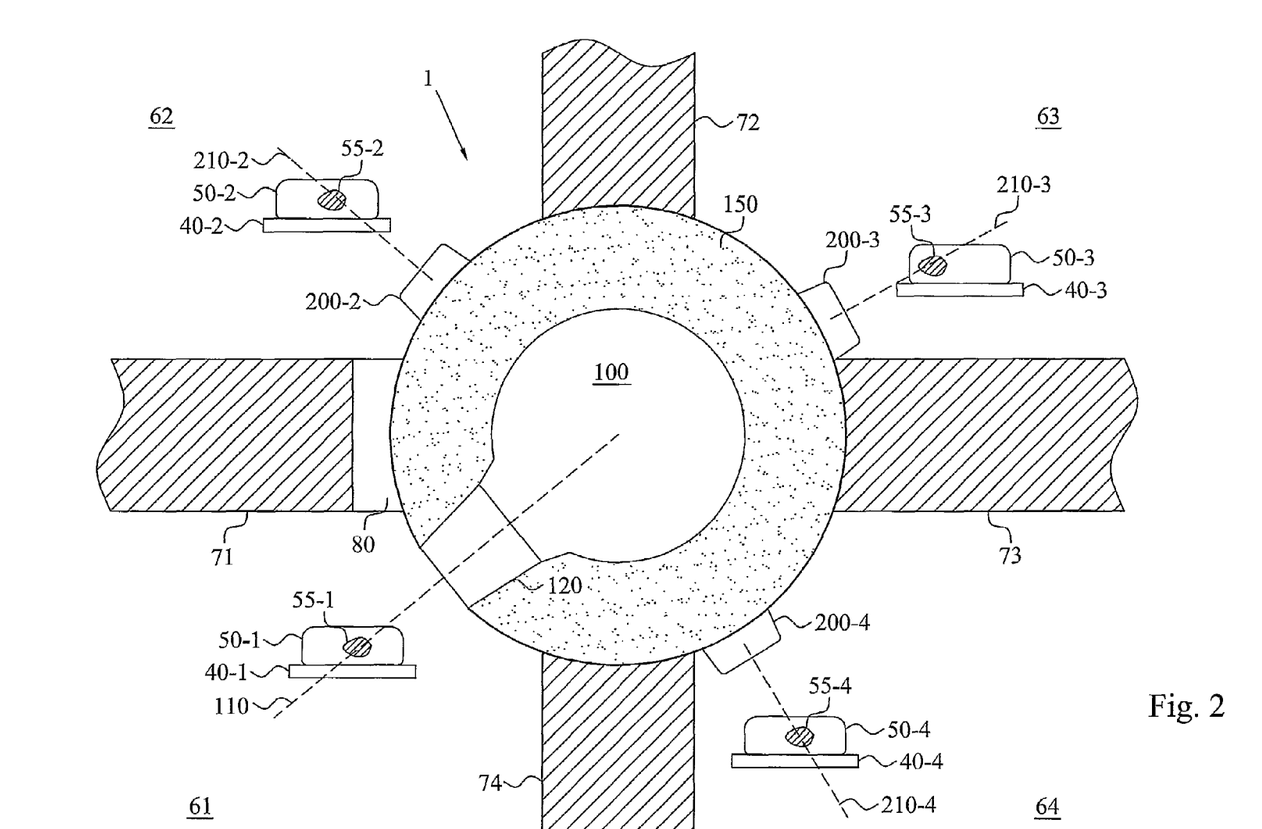
FIG. 2 schematically illustrates an embodiment of a radiation system according to the present invention with an excentric gantry surrounded by multiple treatment rooms.

FIG. 2 schematically illustrates a radiation system or machine 1 of the invention with an excentric gantry 100 that is able to irradiate subjects or patients 50-1 to 50-4 in four different treatment rooms 61 to 64. Thus, the radiation gantry is arranged in connection with these four treatment rooms 61 to 64. In this embodiment, the gantry 100 is positioned in the intersection of the separating members, i.e. the walls or partitions 72, 74 and the ceiling/floor 71, 73, separating the four rooms 61 to 64. Note thus, that the treatment rooms 61 and 64 are positioned one floor beneath the treatment rooms 62 and 63.

The separating members 71 to 74 separating the relevant treatment rooms 61 to 64 have radiation-shielding properties. Thus, the separating members 71 to 74 preferably prevent the treatment radiation beam 110 from leaking from the currently irradiated treatment room 61 to the other treatment rooms 62 to 64. As a consequence of these radiation-shielding separating members 71 to 74, (medical) personnel and patients can safely be present in a treatment room 62 to 64 even when the radiation system 1 irradiates 110 a patient 50-1 in an adjacent treatment room 61. In other word, the separating members 71 to 74 stop (absorb) the treatment radiation 110 so that the leaking radiation levels in the adjacent treatment rooms 62 to 64 are within defined safety margins. The choice of material and material thickness to use for the separating members 71 to 74 depend on properties of the employed treatment radiation 110, e.g. the energy level of the treatment beam 110, the type of radiation used, etc., and can be non-inventively determined by the person skilled in the art. Suitable materials for the separating members 71 to 74 include, but are not limited to, concrete, borated polyethylene and lead. Also the material surrounding and enclosing the radiation transport system, guiding the radiation into the radiation head 120, preferably has good radiation-shielding properties.

The radiation gantry 100 typically has a spherical or cylindrical design, allowing a radiation head 120 to rotate in a dedicated spacing in the walls 72, 74 and ceiling/floor 71, 73.

In the figure, the gantry 100 is directed to irradiate 110 a target volume 55-1 in a first patient 50-1 positioned on a treatment couch 40-1 in a first treatment room 61. The radiation system 1 preferably also comprises a radiation shielding 150, preferably a rotary radiation shielding, and bending magnet (see FIGS. 7-11) to deflect the radiation beam 110 into the currently used treatment room 61 and prevent it from reaching the other treatment rooms 62 to 64.

In addition, the treatment rooms 61 to 64 preferably comprise or have access to simulator heads 200-2 to 220-4 with a light optical and/or X-ray system that is able to simulate the therapeutic beam 110. These simulator heads 200-2 to 200-4 could be arranged and move on a rail just outside of the shield 150. Thus, in the rooms 61 to 64, the low cost simulator 200-2 to 200-4 could be used for patient set-up before the radiation head 120 is turned into the treatment room for treatment operation. It is anticipated by the present invention that these simulator heads 200-2 to 200-4 instead, or alternatively, can be employed for treatment follow-up purposes.

In the figure, three patients 50-2 to 50-4 are positioned on a respective treatment couch 40-2 to 40-4 and are currently subject to a treatment set-up (follow-up) and simulation procedure using the simulator heads 200-2 to 200-4 and simulator beams 210-2 to 210-4. In order to obtain maximum accuracy in the patient set-up (typically within 0.5-1 mm), a stereotactic treatment couch 40-1 to 40-4 is preferably used in the treatment rooms 61 to 64. Such a couch 40-1 to 40-4 is then automatically positioned and individually adjusted to each patient 50-1 to 50-4. Note that in the present invention one and the same couch 40-1 to 40-4 can be used both for the patient set-up (and follow-up) procedure and the treatment and diagnostic imaging activities.

It could be possible that the treatment rooms 61 to 64 are equipped with one simulator head 200-2 to 200-4 each. Alternatively, two or more rooms 61 and 62 could share a single common simulator 200-2. In such a way, the simulator 200-2 is preferably able to move, e.g. by means of a rail system, in a dedicated gap 80 in the floor/ceiling 71 (or wall) separating the rooms 61 and 62.

Figure 3:
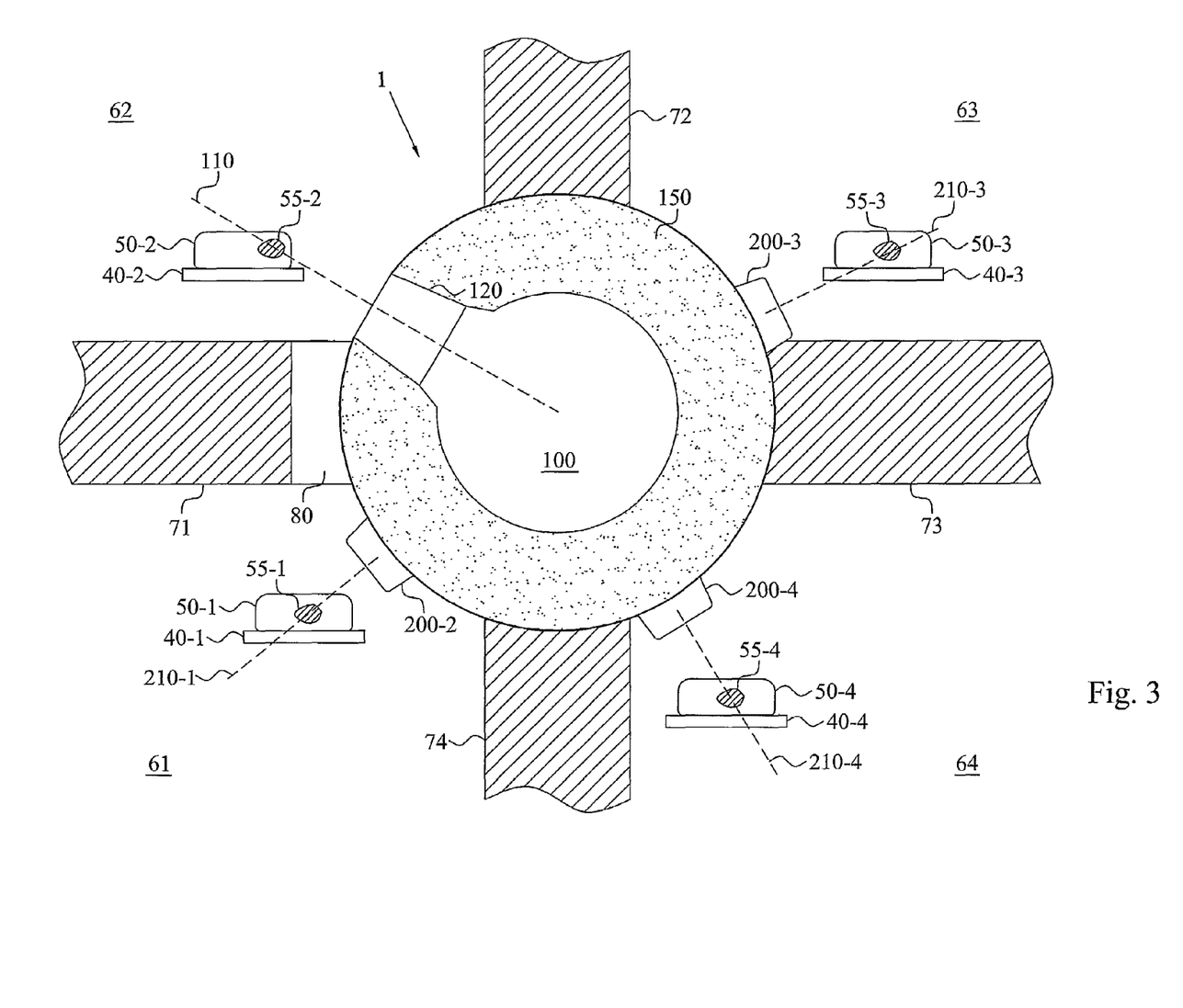
FIG. 3 schematically illustrates the radiation system of FIG. 2 irradiating a patient in another treatment room compared to FIG. 2.

Once, the first patient 50-1 is treated and the set-up and simulation procedures are finished in another room, the gantry 100 may be turned so that the radiation head 120 now can deliver radiation doses to another patient 50-2 in another treatment rooms 62. This scenario is illustrated in FIG. 3, where the radiation head 120 (and possibly the gantry 100) has been rotated to irradiate a target volume 55-2 of a second patient 50-2. The simulator head 200-2 of the room 62, where the patient 50-2 currently is being irradiated using the treatment beam 110, is moved away either to one side of the room 62 in order to allow the radiation head 120 to irradiate the patient 50-2 or to the neighboring treatment room 61 for usage therein in treatment simulation. In the first room 61, a new patient 50-1 may be positioned on the couch 40-1 and a set-up procedure and simulator using a simulator head 200-2 can be performed. Alternatively, a treatment follow-up and subsequently patient exit procedure can be performed involving the previously irradiated patient.

Generally, the sequence of events taking place in a given treatment room is as follows. Firstly, the equipment (couch and radiation and positioning equipment) in the room is readjusted in order to prepare for a next patient to be treated. A patient set-up is then conducted where the patient is accurately positioned on a couch, preferably a stereotactic couch, using different patient positioning systems, e.g. laser-based positioning systems, such as a patient positioning system described in the international patent application WO 2004/000120. Once the patient is accurately positioned on the (stereotactic) couch, a treatment simulation is then performed. During this simulation a light optical and/or diagnostic X-ray system in a simulator head of the radiation system of the invention is used. Thereafter the actual treatment can be performed.

Since the treatment set-up normally can take at least 5 to 10 minutes and the actual treatment of the patient is much quicker, about 1-2.5 minutes, the treatment rooms 61 to 64 and patients 50-1 to 50-4 will generally have access to the therapeutic beam about every 10 minutes. For the gantry design of FIGS. 2 and 3 this implies that up to (and sometimes, especially for simple treatment, more than) 6×4=24 patients can be treated per hour in a very busy therapy center, and still allowing ample set-up time and patient care in each treatment room 61 to 64. This should be compared to the corresponding capacity of a prior art (isocentric) radiation machine, which typically maximally can treat up to 4 to 6 patients during that one hour time period. In addition, in this embodiment of the invention, a single radiation gantry with a single beam transport and scanning system can be employed for both treatment radiation and treatment set-up and simulation in multiple treatment rooms.

Very many different room configurations can be anticipated from the basic four rooms configuration illustrated in FIGS. 2 and 3. Depending on which quadrant a treatment room is located around the central excentric gantry, typically 30-60° oblique lateral anterior (room 61 and 64) or posterior (room 62 and 63) beam directions are possible. With light ions it is very convenient to treat a patient requiring 2-4 beam portal directions in his treatment plan by one beam portal per day and, thus, sequentially use the different treatment rooms of FIGS. 2 and 3 as required by the beam directions. Thus, one and the same patient can, at different irradiation occasions, be irradiated in different treatment rooms, thereby receiving a treatment radiation beam from different incident angles and directions.

Figure 4:
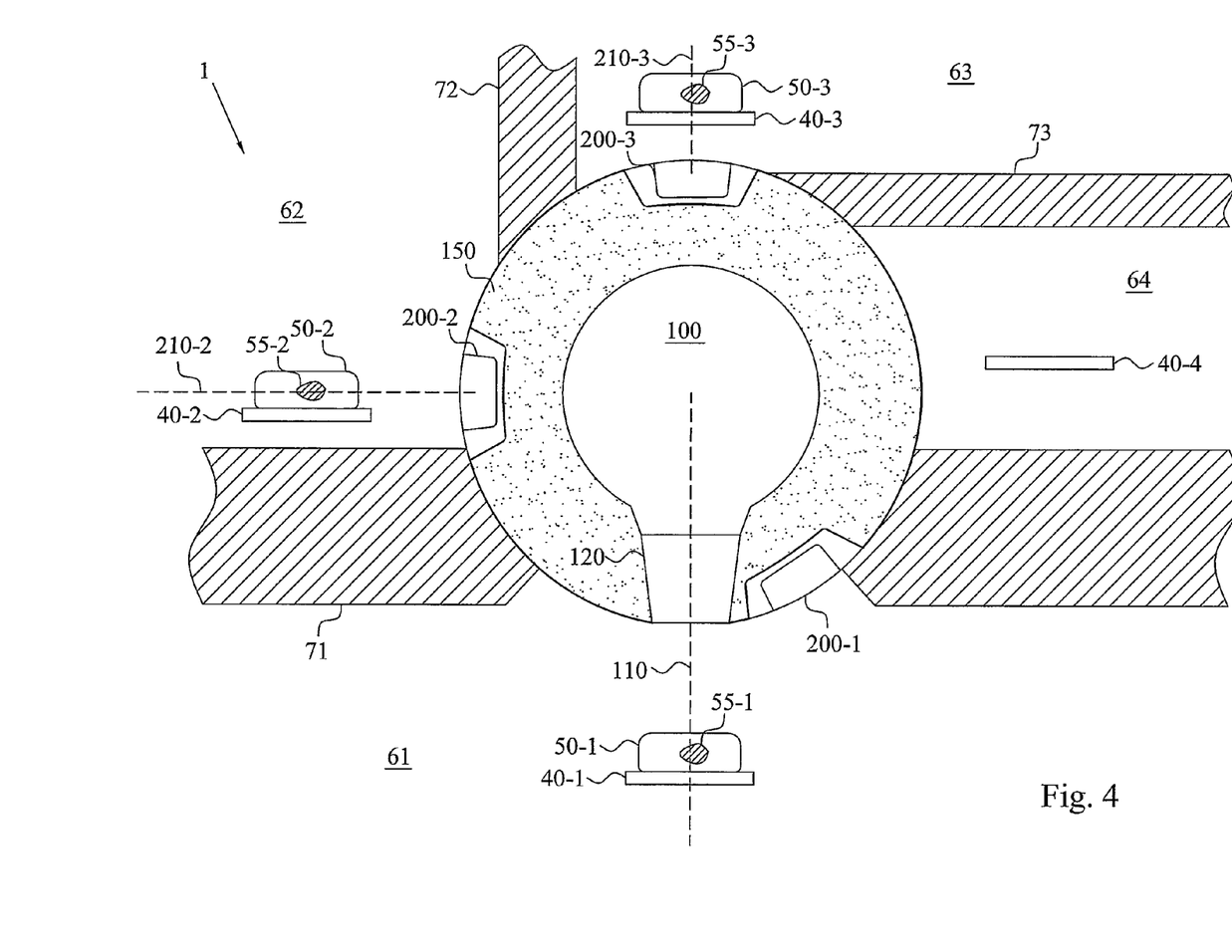
FIG. 4 schematically illustrates another embodiment of a radiation system according to the present invention with an excentric gantry with a different treatment room structure allowing vertical and horizontal beam delivering.

It is also possible to have straight vertical and/or horizontal treatment beams in some rooms, possibly at the same time as other rooms use obliquely incident beams. FIG. 4 schematically illustrates this situation with four different treatment rooms 61 to 64 having access to one common radiation system 1 with excentric gantry design 100 according to the invention. Due to the position of the gantry 100 in the ceiling 71 relative a patient 50-1 on a couch 40-1 in room 61, straight vertical treatment beams 110 are possible. Similarly, for a patient 50-3 in the treatment room 63 posterior vertical beams are possible. However, in another treatment room 64 the beams will obliquely incident into a patient. In the figure, the patient support 40-4 of this room 64 is empty, schematically illustrating the principle with the patient entry/exit procedure.

Correspondingly, if the radiation system 1 and the gantry 100 basically are arranged in a wall 72 between treatment rooms 62 and 63, a patient 50-2 may be vertically irradiated. It is anticipated by the invention that an excentric gantry and radiation system of the present invention could be adapted for only radiating horizontally, only vertically, only obliquely or a combination of horizontally, vertically and/or obliquely.

In this embodiment of the invention, the simulator heads 200-1 to 200-3 have been arranged in dedicated hollows or portions of the gantry 100 or in the radiation shield 150 of the gantry 100. These hollows may be fixed but is preferably movable or rotatable so that the simulator heads 200-1 to 200-3 can be moved away (possible between the rooms 61 to 64) to allow space for the radiation head 120 to irradiate a patient.

It is also possible to combine vertical, anterior and posterior beams in an excentric gantry with six surrounding treatment rooms by combining the solutions from FIGS. 2 or 3 and 4. Such a gantry design results in both oblique lateral anterior and posterior beams in four treatment rooms as well as parallel opposed vertical beams in two rooms.

Figure 5:
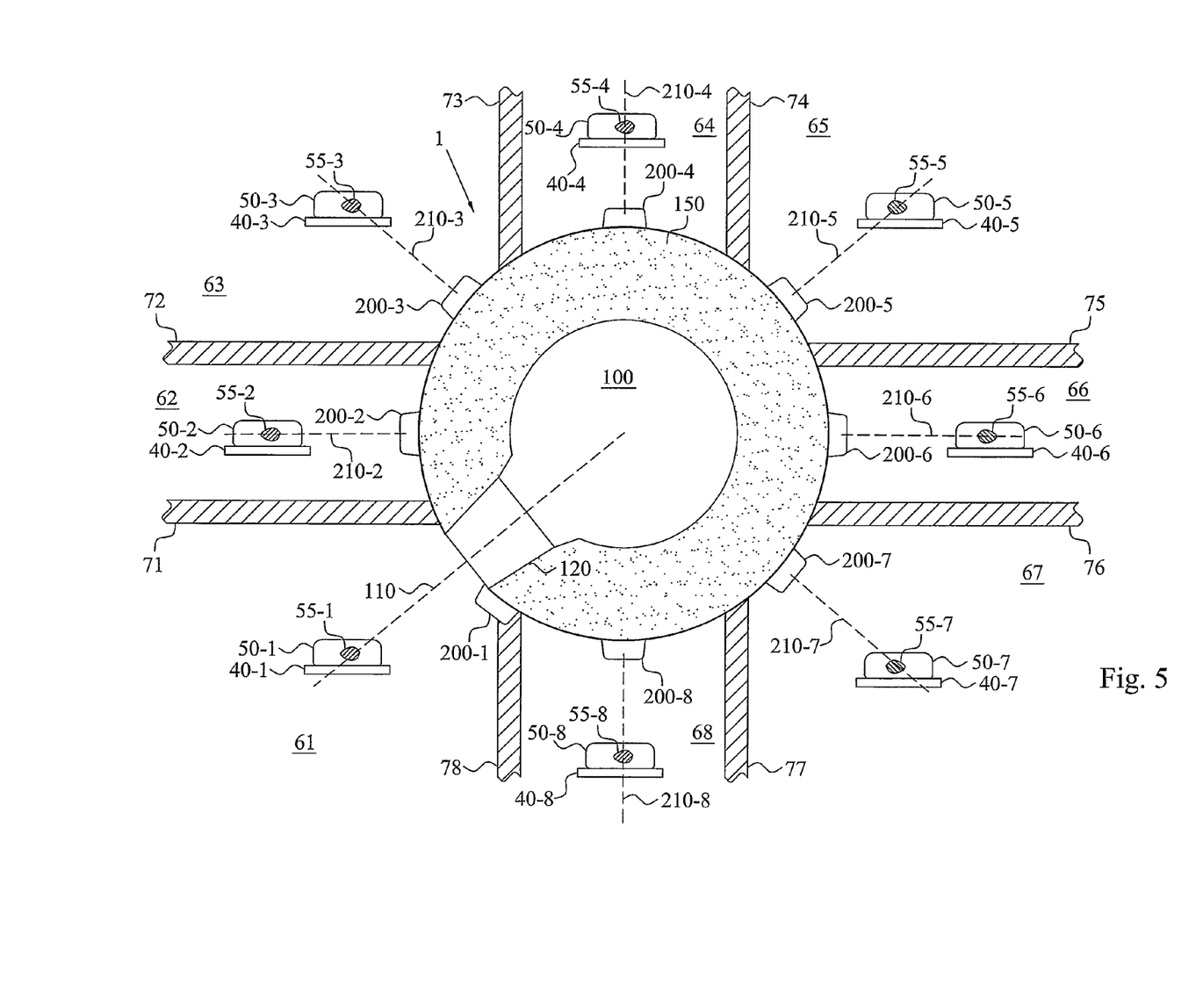
FIG. 5 schematically illustrates a further embodiment of a radiation system according to the present invention with an excentric gantry with a different treatment room structure allowing oblique, vertical and horizontal beam delivery.

FIG. 5 is an illustration of a radiation system 1 and excentric gantry 100 according to the present invention that are able to provide (treatment) radiation 110 in multiple radiation treatment rooms 61 to 68 positioned in up to three different floors. Thus, three treatment room 61, 67, 68 are in a first floor, a second floor includes two treatment rooms 62, 66 with the radiation gantry 100 basically positioned therebetween. A third floor then includes the remaining three treatment rooms 63 to 65. In this embodiment, the gantry 100 is arranged in connection with two radiation-shielding wall-pairs 73, 78 and 74, 77 and two radiation-shielding ceiling-floor pairs 71, 76 and 72, 75 separating the eight treatment rooms 61 to 68. As a consequence, up to seven patients 50-2 to 50-8 can be involved in treatment set-up, simulation or follow-up procedures, possibly employing radiation simulation or diagnosing heads 210-2 to 210-8, simultaneously as a patient 50-1 is irradiated using the treatment radiation beam 110 of the radiation system.

It is also possible to rotate a patient 180° in the horizontal plane in a given treatment room, such as in room 61 in FIG. 5, to obtain during one treatment session a pair of anterior oblique and lateral beam portals on the tumor. This is one of the most efficient treatment configurations for shallow to half deep tumors. For deep therapy, parallel opposed anterior-posterior beams may be most efficient, particularly with higher LET (Linear Energy Transfer) ions like carbon and oxygen, as could be effectively delivered in rooms 64 and 68 of FIG. 5.

Figure 6:
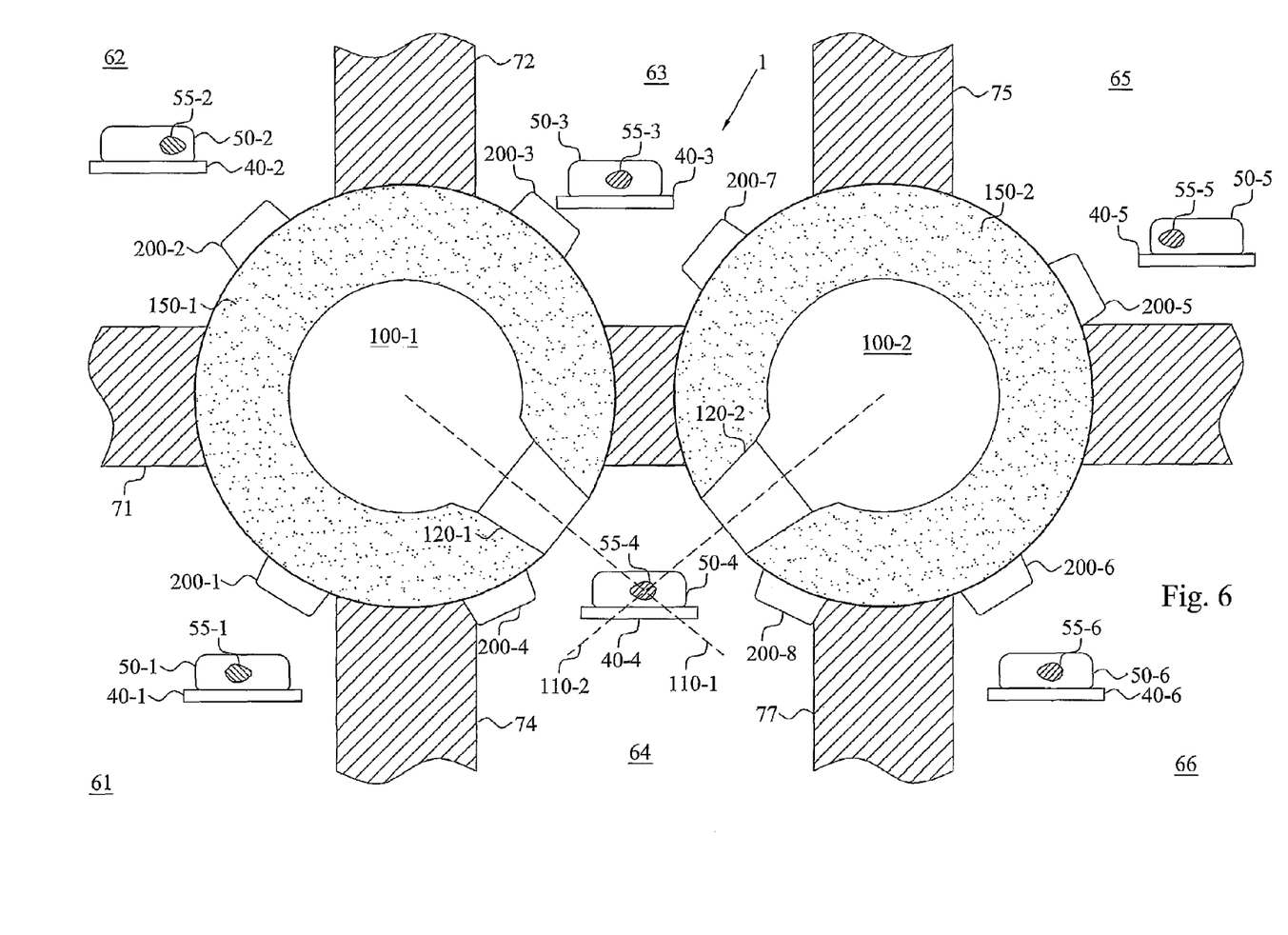
FIG. 6 schematically illustrates yet another embodiment of a radiation system according to the present invention with two excentric gantries allowing two beams to be delivered simultaneously in an treatment room.

With reference to FIG. 6, it is even possible to use a radiation system 1 with multiple, i.e. at least two, excentric gantries 100-1 and 100-2 in such configuration that multiple treatment portals can simultaneously be directed onto one and the same patient 50-4 either as oblique lateral (as in the figure), parallel opposed and/or perpendicular beam combinations 110-1 and 110-2. Thus, in the configuration of FIG. 6, patients 50-3 and 50-4 in room 63 and 64 can be irradiated with beams 110-1 and 110-2 from the radiation heads 120-1 and 120-2 of the two excentric gantries 100-1 and 100-2. In the figure, the remaining four rooms 61, 62, 65 and 66 only have access to one of the gantries 100-1 or 100-2. It is anticipated by the invention that more than two excentric gantries according to the present invention may be arranged in a common configuration so that at least two or more gantries are able to irradiate a patient in one of the treatment rooms. It is also possible, by changing the arrangement of the gantries in the walls and ceiling/floor, to combine the gantry arrangement of FIG. 4 with the arrangement in FIG. 6.

The incident radiation to these at least two gantries of the radiation system of the present invention can originate from different radiation sources. Alternatively, a common radiation source, possibly including an ion source, accelerator system (with a synchrotron or cyclotron), beam guiding and splitting system, can be used for the at least two gantries. An example of a suitable ion source, accelerator and beam guiding system that can be used according to the present invention is disclosed in the patent specification U.S. Pat. No. 6,683,318. The beam splitting system can be realized by a septum, e.g. in the form of a thin conducting foil, arranged in the path of the beam. By applying a (high) current to the septum, the resulting induced magnetic field can be used to divide the incoming ion beam into at least two outgoing ion beams. Each such outgoing beam can be brought, via a beam guiding system, to a respective excentric gantry of the invention, e.g. as illustrated in the configuration of FIG. 6.

The radiation system of the present invention could be designed so that the radiation gantry is static and the radiation head is movable (rotatably) attached to this static gantry to be able to move (rotate) between the multiple treatment rooms. In an alternative embodiment of the present invention, the gantry could include a static gantry part or portion and a movable gantry part or portion. The radiation head is then mechanically supported by the movable gantry part. In such a case, the static gantry part could be attached to or in connection with the separating members of the treatment rooms. In such a design, the movable gantry part and radiation head are movable (rotable) relative the static gantry part (and the separating members) between the treatment rooms.

In FIGS. 2-6, the radiation system according to the present invention has been disclosed with reference to arranging the radiation gantry in connection with a separating member separating at least some treatment rooms positioned at different floors (levels). However the present invention is not limited thereto. For example, the gantry of the radiation system can be arranged in the (radiation-shielding) partition separating two treatment rooms positioned on the same floor. In such a case, the radiation system can direct a radiation beam into at most two different treatment rooms. However, a stand-alone gantry with a general cylindrical or column- or pillar-like design positioned in a large room or hall is also possible. In such a case, this large room can be screened or divided into multiple irradiation stations or (smaller) rooms, separated by radiation-shielding separating members (partitions). Thus in this embodiment, a respective first short end of the separating members is connected to or at least close to the lateral surface of the cylindrical gantry. The separating members then protrude (possibly radially) from the gantry to define the different radiation-shielded treatment rooms. The radiation head can be rotatably attached to the gantry or the radiation head and the movable gantry part is rotatably attached to the static gantry part, in turn arranged on the floor. Depending on the height of the patient couches in the treatment rooms and the output angle of the radiation beam, oblique or horizontal irradiation is then possible.

Figure 7:
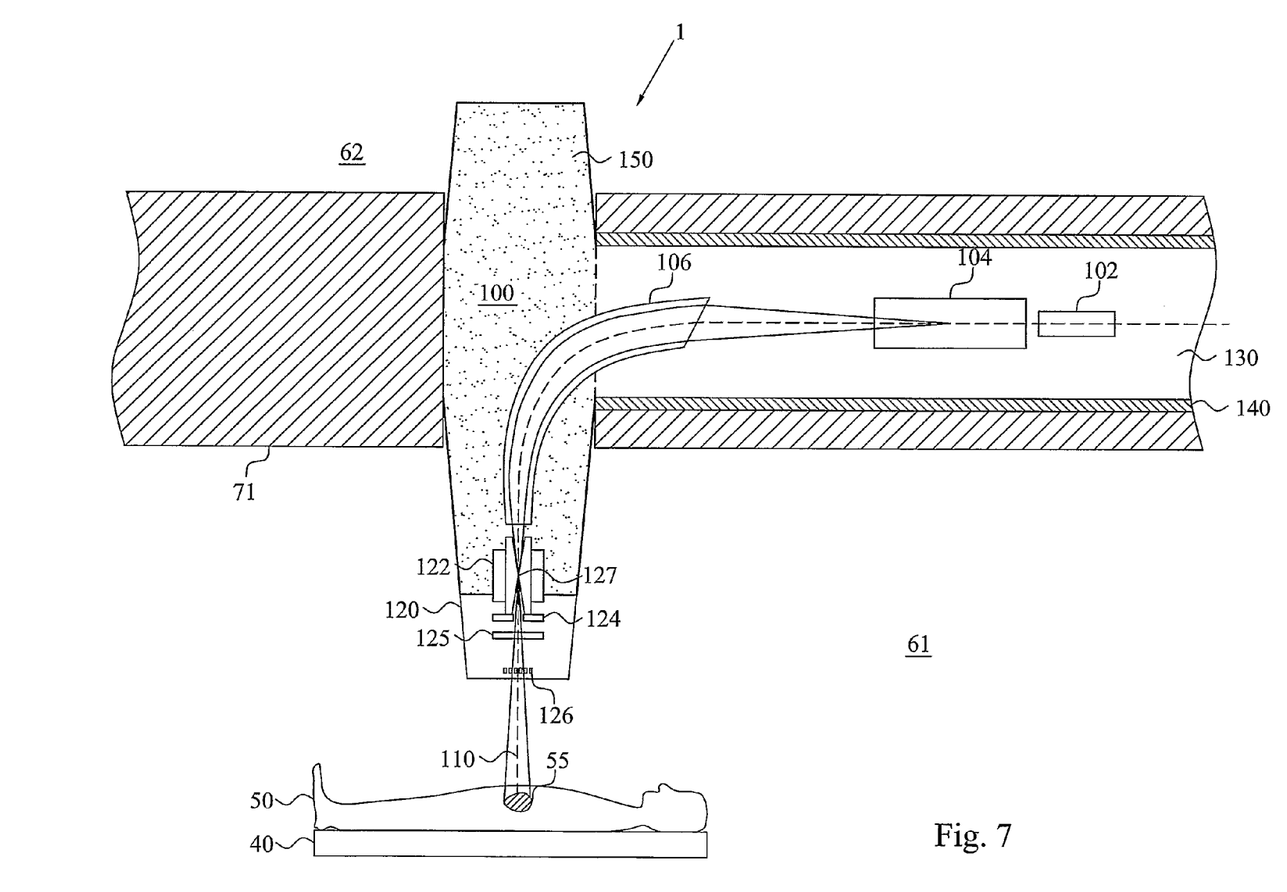
FIG. 7 is a cross section view of an embodiment of an excentric gantry of the radiation system according to the present invention.

FIG. 7 illustrates a perpendicular cross section view of an embodiment of a radiation system 1 with an excentric gantry design 100 of the invention. The incident radiation beam may come from a nearby located radiation source, such as a radiation source arranged in a room next to the gantry 100 and using bending magnets to direct the radiation into the gantry. It is also possible to use a radiation source that is arranged directly on the gantry 100, or a relatively far-placed radiation source, e.g. synchrotron, (see e.g. U.S. Pat. No. 6,683,318) or cyclotron, that can deliver the required radiation to several different treatment units and excentric gantries 100.

Herebelow the invention will be described with reference to a radiation therapy system comprising a (pencil) beam scanning system 104-106, 122 for irradiating a patient 50. Thus, magnetic fields provided by the scanning system 104-106, 122 are used to control the charged particles in the radiation beam. In this beam controlling, the spot-size of the beam can be adjusted and scanned over a treatment area in the patient 50. By a variation of the scanning speed and the beam intensity any desired dose distribution within the target volume 55 can be generated with a minimum extra dose delivered to healthy tissue. However, the invention is not limited to such pencil-like radiation therapy systems and scanning techniques.

According to a preferred embodiment of the invention, the incident radiation beam from the (remote) radiation source (not illustrated) first enters quadrupoles 102 for focusing the beam. Thereafter, the beam preferably enters a scanning magnet 104. This magnet 104 deflects the beam and gives it a scanning motion in the plane of the drawing. The beam emerges from the scanning magnet 104 as if it came from an effective scanning center typically near the middle of the magnet 104. The beam scanning in the plane of the drawing is then bent or deflected in a bending or deflecting magnet 106 for directing the incident beam down to the radiation head 120 and subsequently into the target volume 55 of a patient 40. The bending magnet 106 could be laminated to allow fast field changes between accelerator pulses but also super-conducting to minimize the bending radius.

Due to the beam bending functionality of the magnet 106, the beam enters the radiation head 120 and a second scanning magnet 122. This magnet 122 has the ability to scan or deflect the beam in a plane transversal to the plane of the drawing, i.e. in and out of the plane of the drawing. The beam could then enter a collimator 124 that is arranged to prevent radiation outside the intended scanning beam to continue down to the patient 50. An optional transmission monitor 125 could be provided below the collimator 124 for registering the amount radiation passing from the collimator 124.

The scanning system of FIG. 7 could also be switched off to use a regular dual or single scattering foil system in order to get simple uniform beams.

Before the radiation beam 110 leaves the radiation head 120 it preferably passes a second collimator 126. This collimator 126 is preferably of a multi-leaf collimator type. Such a multi-leaf collimator type comprises a plurality of pairs of opposed elongated, curved or flat, in cross-section wedge shaped leaves, each adjacent leave arranged side by side and such that a fan-shaped configuration which converges towards an apex of the effective radiation source 127. Contrary to the present invention with preferably a single source 127 conventional scanning systems with two consecutive dipole scanning magnets will have different effective source locations in the two scanning planes. The leaves of the collimator 126 are mounted for (combined) rotational and/or translational movement. This dynamic multi-leaf collimator 126 can be used to protect normal tissues lateral to the tumor, i.e. the target volume 55, at the same time as the magnetic field of the bending magnet 106 is rapidly adjusted to the energy required at each scan position. Normally, the energy remains fixed during the scanning of the beam 110 at a certain depth in the patient 40.

The scanned beam 110 typically covers a 30 cm×30 cm field size on the patient 40. If a transmission monitor 125 is provided in the radiation head 120, this monitor could continuously follow and interlock the motion of the scanned beam.

The radiation machine 1 of the invention with an excentric gantry design as illustrated in FIG. 7 is well adapted for usage of a radiation beam of light ions, i.e. from protons and upwards, e.g. helium, carbon or oxygen ions. Such ions are very effective in treating patients with cancer disease. Since they have favorable physical and biological properties that can be exploited for developing improved treatment techniques in comparison to conventional proton beams, light ion beams offer a unique combination of several advantages including a high physical selectivity and higher biological effectiveness in the Bragg peak.

As is well known in the art, light ions require very large bending radii (up to several meters). Prior art radiation gantries and machines providing light ion dose delivery suffer from high installation cost. In addition, such prior art machines have several large sized bending magnets and their pool gaps, which are required to scan the beam in both planes before the bend and obtain a gantry adapted for delivering ion beams in arbitrary orientations in the treatment room. However, the bending magnet 106 used in the present invention can have a small gap and smaller radius and consequently smaller overall size than the prior art used magnets. This results in a compact pencil beam scanning system comprising the scanning and bending magnets 104, 106, 122 that can provide (30 cm×30 cm) beams to several treatments rooms placed around the excentric gantry 100.

Although the gantry design is suitable for usage with light ion radiation it can also be used for any charged particle or even neutral particles like neutrons and photons by first scanning the primary deflected proton or deuteron and electron beams to generate scanned neutral beams, see e.g. the patent specification U.S. Pat. No. 4,442,352.

In FIG. 7, the gantry 100 has a static gantry part 140 attached to the floor/ceiling 71 separating the two adjacent treatment rooms 61, 62. An inner movable gantry part 130 with attached or integrated radiation 120 is movably, here rotatably, supported by the static part 140. This movable support can be realized using conventional gear solutions and bearings. In order to increase the stability of the gantry 100, the radiation head 120 can be supported by the movable gantry part 130 the right-hand side (as illustrated in the figure) and to the left-hand side. In such a case, the gantry 100 typically would include two static parts 140, each arranged in the floor/ceiling 71 but on either side of the rotating radiation head 120.

Figure 8:
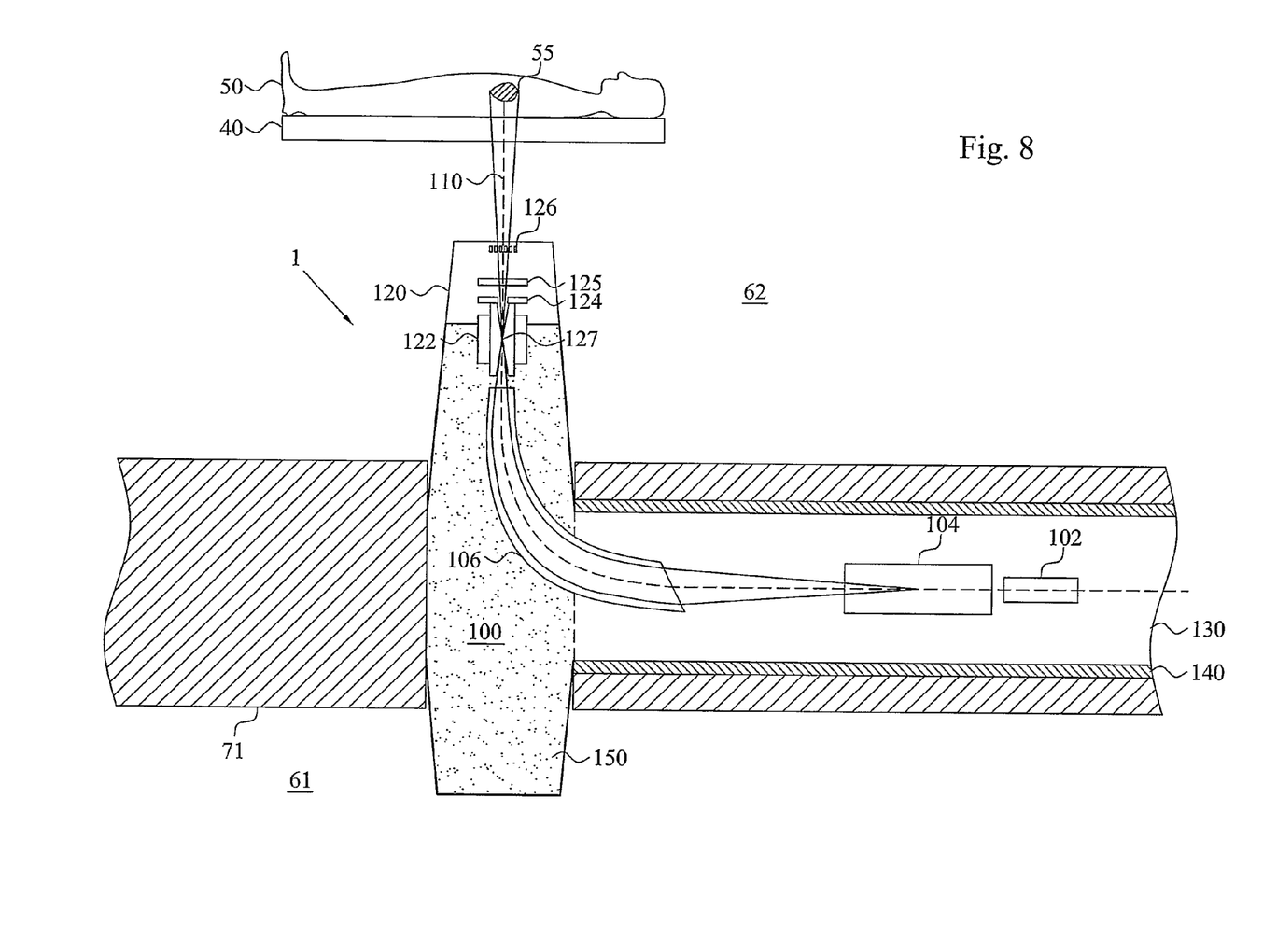
FIG. 8 illustrates the radiation system of FIG. 7 irradiating a patient in another treatment room compared to FIG. 7.

When the radiation machine is to be used for treating a patient in another treatment room 62, the gantry 100 (the movable gantry part 130) is simply turned or rotated, thus resulting in a rotation of the scanning and bending system 102-106, 122 and the radiation head 120. FIG. 8 illustrates this principle, where the excentric gantry 100 of the radiation system 1 of FIG. 7 is turned from irradiating a patient in a first treatment room 61 to irradiating a second patient 50 lying on a treatment couch 40 arranged in a second treatment room 62. As is seen in the figure, due to the rotation of the gantry 100, the bending magnet 106 now directs the incident beam towards this second treatment room 62. In this way a single scanning, collimation, beam bending and angular adjusting system can be used in several treatment rooms, which significantly reduces the cost for the whole installation.

Figure 9:
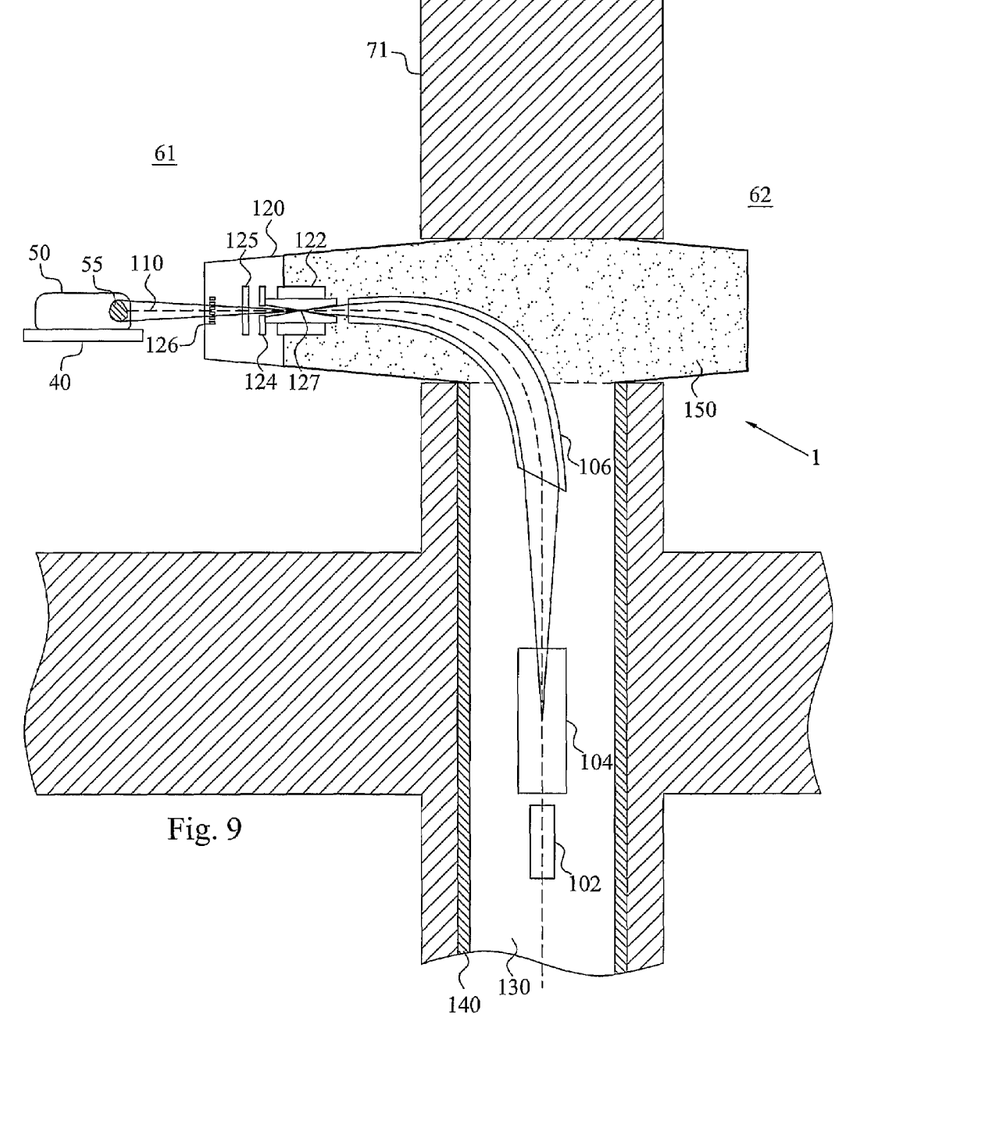
FIG. 9 is a cross section view of another embodiment of an excentric gantry of the radiation system according to the present invention.

FIG. 9 is a corresponding cross-sectional illustration of another embodiment of a radiation system according to the present invention. In this embodiment, the gantry 100 is mainly arranged in a radiation-shielding wall or partition 71 separating two neighboring treatment rooms 61 and 62. This gantry embodiment 100 is in particular configured for providing horizontal beams 110 to the treatment volume 55 of the patient 50. The including units 124-126 of the radiation head 120 and the beam processing (guiding and scanning) system 104-106, 122 are similar to the corresponding units discussed above in connection with FIG. 7 and are not further described.

Although the rotation axes of the excentric gantries illustrated in FIGS. 2 to 8 are horizontal or vertical as illustrated in FIG. 9, the present invention is not limited thereto. The rotation axis can have any angle from vertical to horizontal, somewhat dependent on how the beam is extracted from the accelerator and the range of variability needed clinically.

Figure 10:
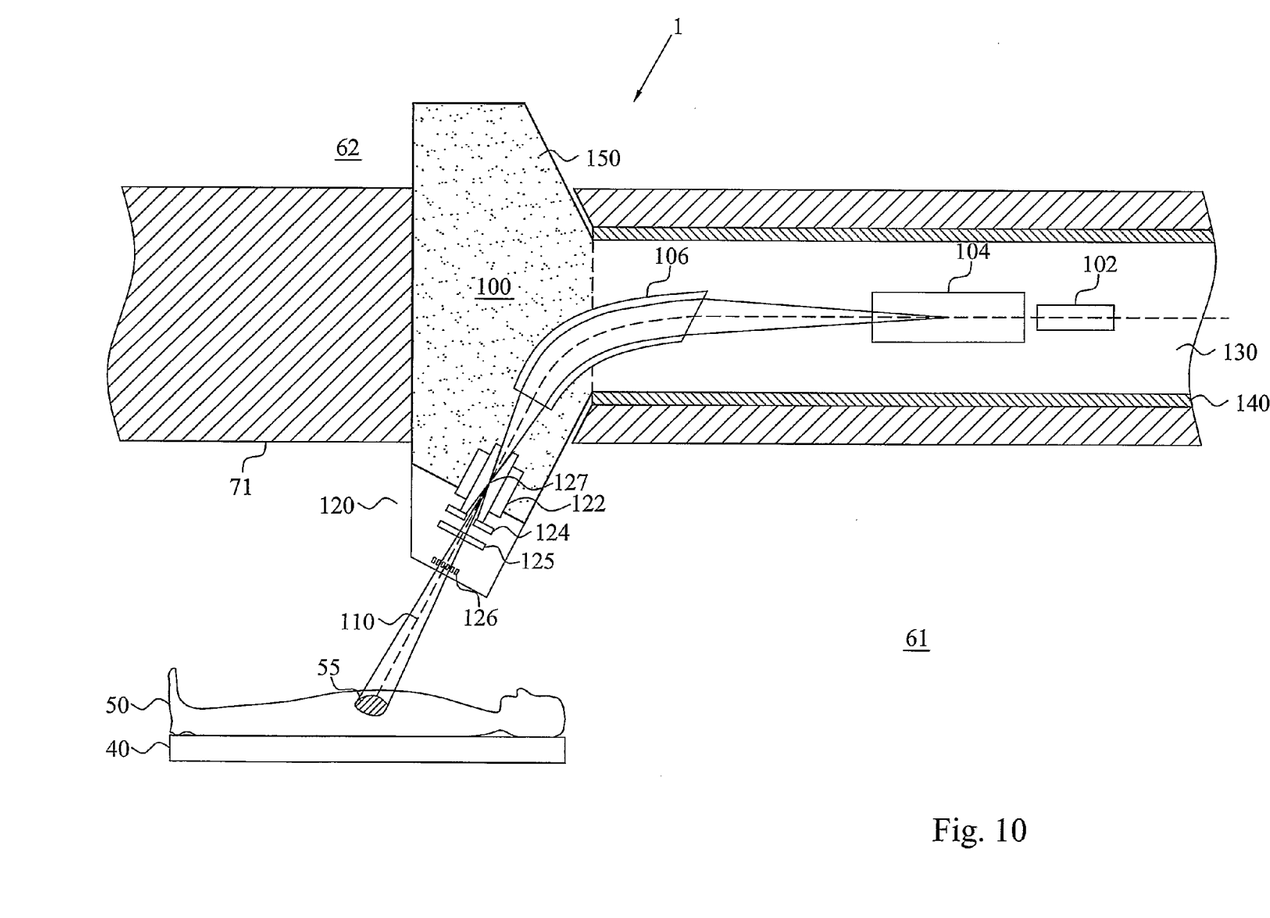
FIG. 10 is a cross section view of a further embodiment of an excentric gantry of the radiation system according to the present invention.

FIG. 10 illustrates a cross-section of a portion of radiation system 1 with a gantry 100 providing oblique beams 110. Compared to the radiation system of FIG. 7, in the present embodiment the treatment beam 110 is deflected by the bending magnet 106 less than 90° in order to save power and to get oblique beams in multiple treatment rooms 61 and 62. Angles as low as 30° up to some 60° could be useful in special cases.

The including units of the gantry 100 and radiation system 1 correspond to the units discussed above in connection with FIG. 7.

Figure 11:
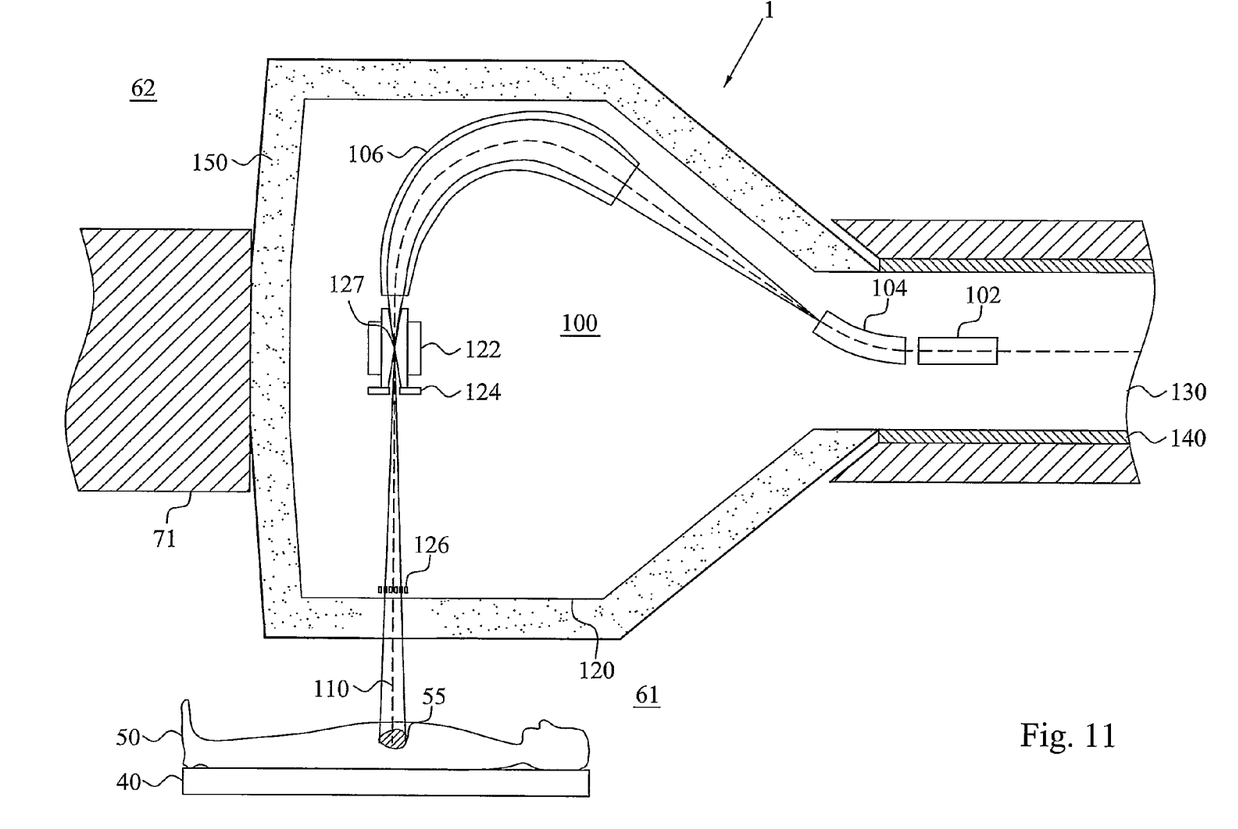
FIG. 11 is a cross section view of yet another embodiment of an excentric gantry of the radiation system according to the present invention.

FIG. 11 illustrates another possible design of the internal units of the beam scanning and bending system 104-106, 122 of the excentric gantry 100 of the present invention. This embodiment minimizes the diameter of the rotary gantry part 130 including the magnet 106 and treatment head 120. Similarly to the embodiment illustrated in FIGS. 7 to 10, the incident (light ion) radiation beam, preferably, first enters quadrupoles 102. The beam then enters a bending and scanning magnet 104 that scans the beam in the plane of the drawing. The scanned beam is then bent in a (super-conducting) bending magnet 106. The bending magnet 106 preferably directs the beam into a second scanning magnet 122. This scanning magnet 122 and the collimators 124 and 126, where discussed in connection with FIG. 7. In order to really minimize the gantry size and maximize the cost effectiveness, the radiation shielding 150 may also be included, calling for a somewhat smaller deflection in the magnet 104 than shown in the FIG. 11.

It will be understood by a person skilled in the art that various modifications and changes may be made to the present invention without departure from the scope thereof.

The invention claimed is:

1. A radiation system comprising:
    a gantry comprising:
        a static gantry part; and
        a movable gantry part movably supported by said static gantry part;
    a radiation head mechanically supported by said movable gantry part and being movable relative said static gantry part in a dedicated spacing in a radiation-shielding separating member between a first position for directing a radiation beam into a first treatment room and a second position for directing said radiation beam into a second treatment room, said separating member separating at least said first treatment room and said second treatment room; and
    a movable radiation shielding being a part of said movable gantry part and preventing radiation from reaching said second treatment room when said radiation head is in said first position and preventing radiation from reaching said first treatment room when said radiation head is in said second position.

2. The radiation system according to claim 1, wherein said static gantry part is adapted for arrangement in a radiation-shielding separating member.

3. The radiation system according to claim 1, wherein said static gantry part is adapted for partly being arranged in said radiation-shielding separating member separating at least said first treatment room and said second treatment room.

4. The radiation system according to claim 1, wherein said static gantry part is adapted for arrangement in said radiation-shielding separating member separating at least said first treatment room and said second treatment room.

5. The radiation system according to claim 1, wherein said separating member is selected from at least one of:
    a radiation-shielding partition between said first and second treatment room;
    a radiation-shielding ceiling-floor pair between said first and second treatment room, said first and second treatment room being positioned at different floors.

6. The radiation system according to claim 1, further comprising at least one radiation simulation head, said simulation head being able to direct a radiation simulation beam into said first treatment room simultaneously as said radiation head directs said radiation beam into said second treatment room.

7. The radiation system according to claim 6, wherein said radiation simulation head is movable on said gantry between said first and second treatment room.

8. The radiation system according to claim 6, wherein said radiation head is adapted for providing a treatment beam and said radiation simulation head is adapted for providing a treatment simulation beam.

9. The radiation system according to claim 1, further comprising:
    a second gantry adapted for arrangement in connection with at least said second treatment room and a third treatment room separated by a radiation-shielding separating member; and
    a second radiation head mechanically supported by said second gantry, said second radiation head being movable relative said second gantry between a first position for directing a radiation beam into said second treatment room and a second position for directing said radiation beam into said third treatment room.

10. The radiation system according to claim 9, wherein said radiation head and said second radiation head are configured for directing said radiation beams into said second treatment room from different incident angles.

11. The radiation system according to claim 9, further comprising a radiation beam splitter for simultaneously providing radiation from a common radiation source to said first gantry and to said second gantry.

12. The radiation system according to claim 2, wherein said static gantry part is adapted for partly being arranged in said radiation-shielding separating member separating at least said first treatment room and said second treatment room.

13. The radiation system according to claim 7, wherein said radiation head is adapted for providing a treatment beam and said radiation simulation head is adapted for providing a treatment simulation beam.

14. The radiation system according to claim 10, further comprising a radiation beam splitter for simultaneously providing radiation from a common radiation source to said first gantry and to said second gantry.

* * * * *